United States Patent [19]

Rovnyak

[11] 4,266,065
[45] May 5, 1981

[54] MERCAPTOACYLDIHYDROPYRAZOLE CARBOXYLIC ACID DERIVATIVES

[75] Inventor: George C. Rovnyak, Hopewell, N.J.

[73] Assignee: E. R. Squibb & Sons, Inc., Princeton, N.J.

[21] Appl. No.: 140,355

[22] Filed: Apr. 14, 1980

[51] Int. Cl.³ .................................................. C07D 231/06
[52] U.S. Cl. .................................. 548/379; 424/273 P
[58] Field of Search ........................................ 548/379

[56] References Cited

U.S. PATENT DOCUMENTS

| | | | |
|---|---|---|---|
| 4,105,776 | 8/1978 | Ondetti et al. ...................... | 424/274 |
| 4,129,566 | 12/1978 | Ondetti et al. ...................... | 546/326 |
| 4,192,878 | 3/1980 | Ondetti ................................ | 424/270 |
| 4,211,786 | 7/1980 | Rovnyak ............................. | 548/379 |

Primary Examiner—Henry R. Jiles
Assistant Examiner—Natalia Harkaway
Attorney, Agent, or Firm—Lawrence S. Levinson; Donald J. Barrack

[57] ABSTRACT

Compounds having the formula

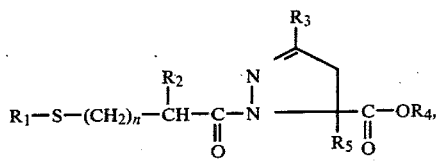

and basic salts thereof, wherein
$R_1$ is hydrogen, alkyl, aryl, arylalkyl or

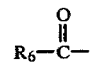

wherein $R_6$ is alkyl or aryl;
$R_2$ is hydrogen, alkyl, trifluoromethyl or pentafluoroethyl;
$R_3$ is hydrogen or alkyl;
$R_4$ is hydrogen, alkyl or arylalkyl;
$R_5$ is hydrogen or alkyl; and
$n$ is 0, 1 or 2;
have hypotensive activity.

8 Claims, No Drawings

MERCAPTOACYLDIHYDROPYRAZOLE CARBOXYLIC ACID DERIVATIVES

RELATED APPLICATIONS

United States patent application Ser. No. 18,547, filed Mar. 8, 1979 discloses mercaptoacylpyrazolidinone carboxylic acid derivatives having the formula wherein $R_1$, $R_4$ and n are as defined hereinafter, $R_2'$ is hydrogen or alkyl, and $R_3'$ is hydrogen, alkyl, aryl or arylalkyl.

United States patent applications Ser. No. 18,548, filed Mar. 8, 1979 and Ser. No. 79,291, filed Sept. 27, 1979, disclose mercaptoacyldihydropyrazole carboxylic acid derivatives having the formula wherein $R_1$, $R_4$ and n are as defined hereinafter, $R_2'$ is hydrogen or alkyl, and $R_3''$ is aryl.

The compounds of the above-described three applications are ACE inhibitors and are useful for the treatment of hypertension in mammals.

BACKGROUND OF THE INVENTION

U.S. Pat. No. 4,105,776, issued Aug. 8, 1978, describes a group of thioalkanoyl derivatives of azetidine-, pyrrolidine- and piperidinecarboxylic acid compounds having the structural formula

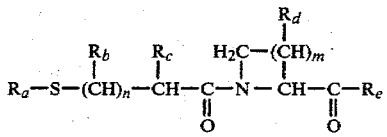

wherein the symbols can be, inter alia, as follows: $R_a$ can be hydrogen, lower alkyl, phenyl, substituted phenyl, phenyl-lower alkyl,

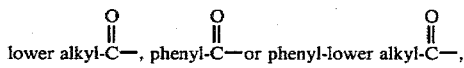
lower alkyl-C—, phenyl-C— or phenyl-lower alkyl-C—, $R_b$ can be hydrogen, $R_c$ can be hydrogen or lower alkyl, $R_d$ can be hydrogen, hydroxy or lower alkyl, $R_e$ can be hydroxy, —NH$_2$ or lower alkoxy, n can be 0, 1 or 2 and m can be 1, 2 or 3.

U.S. Pat. No. 4,129,566, issued Dec. 12, 1978, describes derivatives of dehydrocyclicimino acids having the structural formula

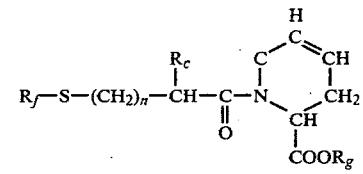

wherein the symbols can be, inter alia, as follows: $R_c$, $R_f$ and $R_g$ can each be hydrogen or lower alkyl and n can be 0 or 1.

U.S. Pat. No. 4,192,878, issued Mar. 11, 1980, describes compounds having the structural formula

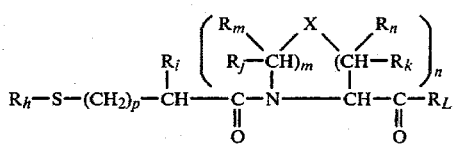

wherein the symbols can be, inter alia as follows: $R_h$ can be hydrogen, lower alkanoyl or benzoyl, $R_i$, $R_j$, $R_k$, $R_m$ and $R_n$ can each be hydrogen or lower alkyl, $R_L$ can be hydroxy or lower alkoxy, m can be 1, 2 or 3, n can be 0, 1 or 2 and m+n can be 2 or 3, p can be 0 or 1 and X can be O, S, SO or SO$_2$, m being 2 and n being 1 when X is O.

The compounds set forth above are disclosed as being useful as inhibitors of the conversion of the decapeptide angiotensin I to angiotensin II, and are, therefore, useful in reducing or relieving angiotensin related hypertension.

BRIEF DESCRIPTION OF THE INVENTION

Compounds having the formula

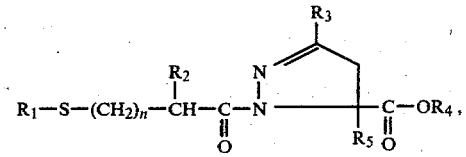

and basic salts thereof, have hypotensive activity. In formula I, and throughout the specification, the symbols are as defined below.

$R_1$ is hydrogen, alkyl, aryl, arylalkyl or

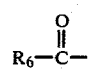

wherein $R_6$ is alkyl or aryl;
$R_2$ is hydrogen, alkyl, trifluoromethyl or pentafluoroethyl;
$R_3$ is hydrogen or alkyl;
$R_4$ is hydrogen, alkyl or arylalkyl;
$R_5$ is hydrogen or alkyl; and
n is 0, 1 or 2.

The term "aryl", as used throughout the specification, either by itself or as part of a larger group, refers to phenyl or phenyl substituted with one, two or three halogen, alkyl, alkoxy, alkanoyl, nitro, amino, alkylamino, dialkylamino, trifluoromethyl, cyano or carboxyl groups. Phenyl is the preferred aryl group.

The term "alkanoyl", as used throughout the specification, either by itself or as part of a larger group, refers to groups having 2 to 9 carbon atoms.

The terms "alkyl" and "alkoxy", as used throughout the specification, either individually or as part of a larger group, refer to groups having 1 to 8 carbon atoms. Alkyl and alkoxy groups having 1 to 3 carbon atoms are preferred.

The term "halogen", as used throughout the specification, either by itself or as part of a larger group, refers to fluorine, chlorine, bromine and iodine.

DETAILED DESCRIPTION OF THE INVENTION

The compounds of formula I are useful as hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one or a combination of compounds of formula I, angiotensin dependent hypertension in the species of mammal suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 300 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methyclothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration or in sterile solutions or suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amound of active substance in these compositions or preparations is such that a suitable dosage in the range indicated is obtained.

The compounds of this invention can be obtained by reacting an amino acid having the formula

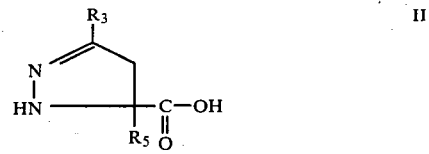

with a small excess of a mercaptoacyl halide having the formula

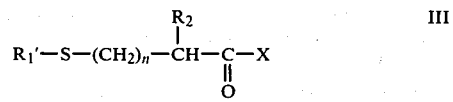

wherein $R_1'$ is alkyl, aryl, arylalkyl,

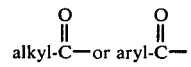

and X is chlorine or bromine, to obtain the corresponding products of formula I wherein $R_1$ is other than hydrogen and $R_4$ is hydrogen; i.e., compounds having the formula

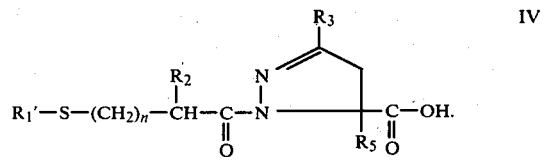

The reaction is preferably run in a two phase solvent system such as water/ether or water/ethyl acetate, in the presence of a base such as an alkali metal hydroxide or alkali metal carbonate. While reaction conditions are not critical, more favorable yields will be obtained if the reaction is run within the following parameters. The ratio of amino acid (formula II) to mercaptoacyl halide (formula III) will preferably be within the range of 1:1.1 to 1:1.5, most preferably within the range of 1:1.1 to 1:1.2. Additional base can be added as needed to maintain the pH of the reaction mixture between about 7.5 and 8.5.

The compounds of formula I wherein $R_1$ and $R_4$ are both hydrogen can be prepared by deacylation of the corresponding compounds of formula IV wherein $R_1'$ is

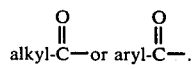

Hydrolysis of the acylthio group can be accomplished by treatment with aqueous base, e.g., ammonium hydroxide or an alkali metal hydroxide.

The compounds of formula I wherein $R_4$ is alkyl or arylalkyl can be obtained by treating the corresponding acid of formula I with the appropriate diazoalkane or with the appropriate alcohol in the presence of a dehydrating agent such as dicyclohexylcarbodiimide and a catalyst such as dimethylaminopyridine. Alternatively, an acid of formula I can be converted first to an acid halide and then reacted with the appropriate alcohol in the presence of an acid acceptor, e.g., an organic base such as triethylamine.

The compounds of this invention wherein $R_4$ is hydrogen form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The non-toxic, physiologically acceptable salts are preferred, although other salts are also useful, e.g., in isolating or purifying the product.

The amino acids of formula II are novel compounds, and as such, they form an integral part of this invention. Those amino acids of formula II wherein $R_5$ is alkyl can be prepared by a two step process. The cycloaddition of a diazoalkane having the formula

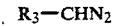  V and an acrylic ester having the formula

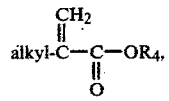  VI yields a 1-pyrazoline derivative having the formula

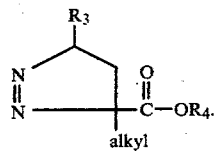  VII

Tautomerization and hydrolysis of a compound of formula VII to a 2-pyrazoline derivative having the formula

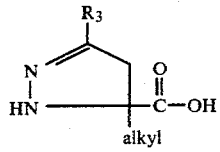  VIII can be accomplished by first treating the 1-pyrazoline derivative with gaseous hydrogen chloride in ether followed by treatment with hydrochloric acid.

Amino acids of formula II wherein $R_5$ is hydrogen can be prepared by reacting a compound having the formula

  IX with a diazoalkane of formula V to obtain a compound having the formula

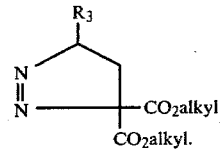  X

Treatment of a compound of formula X with gaseous hydrogen chloride in ether, followed by heating the resulting 2-pyrazoline hydrochloride salt to about 60°–80° C. in hydrochloric acid yields a 2-pyrazoline derivative having the formula

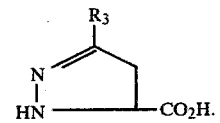  XI

The compounds of formula I each contains at least one asymmetric carbon and accordingly exist in stereoisomeric forms or in racemic mixtures thereof. The above described synthesis can utilize the racemate or one of the enantiomers as starting material. When the racemic starting material is used in the synthetic procedure, the stereoisomers obtained in the product can be separated by conventional fractional crystallization of the diastereomeric salt mixture formed, e.g., with an optically active amine. It is theorized that the activity of the racemic products is due mostly to the S-isomer with respect to the carbon of the amino acid, and this isomer is accordingly preferred.

The following examples are specific embodiments of this invention.

EXAMPLE 1

[1(S),5S]-4,5-Dihydro-1-[3-(acetylthio)-2-methyl-1-oxopropyl]-1$\underline{H}$-pyrazole-5-carboxylic acid (A) Diethyl-3,4-dihydro-5$\underline{H}$-pyrazole-5,5-dicarboxylic acid A solution of 29.3 g of diethyl ethylenemalonate in 300 ml of ether is treated with ethereal diazomethane until a slight yellow color persists. Excess diazomethane is removed on a steam bath, and the solution is then concentrated in vacuo to give 32.5 g of the title compound as an oil.

Analysis calc'd for $C_9H_{14}N_2O_4$: C, 50.45; H, 6.58; N, 13.08. Found: C, 50.34; H, 6.61; N, 12.90.

(B) Diethyl-4,5-dihydro-1$\underline{H}$-pyrazole-5,5-dicarboxylic acid, hydrochloride salt A cold solution of 32.5 g of diethyl-3,4-dihydro-5$\underline{H}$-pyrazole-5,5-dicarboxylic acid in 250 ml of ether is treated with a slight excess of gaseous hydrogen chloride. The product appears as an oil, and slowly crystallizes on standing at room temperature for several hours to give 31.2 g of the title hydrochloride salt, melting point 90°–94° C.

Analysis calc'd for $C_9H_{14}N_2O_4 \cdot HCl$: C, 43.12; H, 6.03 N, 11.17. Found: C, 43.17; H, 6.08; N, 11.21.

(C) 4,5-Dihydro-1$\underline{H}$-pyrazole-5-carboxylic acid

A solution of 18.5 g of diethyl-4,5-dihydro-1$\underline{H}$-pyrazole-5,5-dicarboxylic acid, hydrochloride salt in 72 ml of 1.07 N hydrochloric acid is stirred and heated at 70°–75° C. (oil bath) until evolution of carbon dioxide ceases (6 hours). The solution is cooled, and the water evaporated in vacuo to give 12.0 g of a viscous residue.

To remove the HCl from the above crude product, an aqueous solution is slowly passed through a column of 100 ml of 20-50 mesh Dowex 50W-X8 resin (H+). The strongly acidic initial fractions are set aside for later purification over regenerated resin. The neutral column is treated with 3 N NH$_4$OH. Evaporation of the eluate gives 4.8 g of impure amino acid. An additional 1.5 g of similar material is obtained from the acidic fractions described above (the initial acidic fractions can be significantly reduced in volume by an extended batch slurry of a portion of the resin with the aqueous hydrochloride before placing the resin in the column).

A solution of this material in a small amount of methanol is placed on seven preparative plates (Merck 2 mm) and developed in methanol (6 hours). Of the three UV absorbing areas detected, the center portion contains the desired product, which is obtained by methanol extraction to give 3.45 g of the title compound as an oil.

(D)
[1(S),5S]-4,5-Dihydro-1-[3-(acetylthio)-2-methyl-1-oxopropyl]-1H-pyrazole-5-carboxylic acid The above amino acid is combined with 1.55 g of similarly derived product and dissolved in 40 ml of water. The pH is raised to 8.0 using 1 N NaOH. An equal volume of ethyl acetate is added and the mixture is stirred during the drop-wise addition of a solution of 9.0 g of D-3-(acetylthio)-2-methylpropionyl chloride in 20 ml of ethyl acetate. The pH is maintained between 7.5-8.0 with 6 N NaOH during the one hour procedure. After completion of addition, the pH continues to fall and is kept at the optimum range with the continual addition of base. After 6 hours, the reaction is terminated by separating the ethyl acetate and treating the aqueous portion with 3 N HCl to pH 2.0. Extraction of the resulting oil with ethyl acetate gives 6.6 g of impure product.

Additional product is obtained by combining the original ethyl acetate layer with the extracted aqueous solution and treating this with 6 N NaOH to pH 8.0. An additional 2.0 g of acid chloride is gradually added and the reaction pH is maintained at 7.5-8.0 for 7 hours with the necessary addition of base. The work-up procedure yields 3.1 g of material having the same R$_f$ values as the first fraction.

The above procedure is repeated for a third time (6 hours) without the addition of acid chloride. The yield of impure product is 1.6 g. The three portions are combined.

A small amount of this material is dissolved in ethyl acetate and treated with an equivalent amount of 1-adamantanamine. Conversion of the resulting salt back to the acid gives a homogeneous product.

On the basis of this result, 11.1 g of the impure acylated amino acid is dissolved in 150 ml of ethyl acetate and treated with 6.5 g of 1-adamantanamine. The amine salt immediately precipitates to give 13.1 g of colorless material, melting point 167°-169° C. $[\alpha]D^{20} = -42°$ (MeOH). TLC analysis of a small amount of this material that is converted to the free acid shows that no purification has taken place, and the adamantanamine salt formation can be eliminated from future work. The amine salt (13.1 g) is then dissolved in 25 ml of 3 N HCl and extracted twice with CHCl$_3$. The extracts are combined, dried, and evaporated to give 10.7 g of a wax-like semi-solid mixture. A solution of this material in 15 ml of methanol is distributed equally on ten 7"×7" 2 mm silica gel plates (Uniplate) and developed in methanol-/ethyl acetate (1:1). Of the two UV absorbing portions, the faster moving portion contained 5.7 g of impurity and the slower moving portion contained 3.8 g of a cream colored solid, melting point 170°-175° C. Both products are obtained by methanol extraction.

Elemental analysis of the above solid shows it to be the adamantanamine salt of the acid. A solution of this material in 9 ml of 3 N HCl at room temperature gradually forms 0.84 g of a colorless solid, melting point 100°-102° C. $[\alpha]_{20}{}^D = -180°$ (MeOH). This material is treated with 6 ml of hot methylene chloride, diluted with 15 ml of ether and kept at 5° C. for one hour. After filtration to remove silica gel, the filtrate is diluted with 15 ml of ether and cooled at 5° C. for 3 hours to give 0.04 g of solid, melting point 240°-245° C. The filtrate from the above purification is evaporated in vacuo to yield 0.70 g of a colorless solid, melting point 100-102°; $[\alpha]_{20}{}^D = -183°$ (MeOH). Crystallization from 4.5 ml of hot water yields 0.56 g of desired product, melting point 104°-106°; $[\alpha]_{20}{}^D = -205°$ (MeOH).

Analysis calc'd for C$_{10}$H$_{14}$N$_2$O$_4$S.H$_2$O: C, 43.46; H, 5.83; N, 10.14. Found: C, 43.91; H, 5.74; N, 9.96.

EXAMPLE 2

[1(S),5S]-4,5-Dihydro-1-(3-mercapto-2-methyl-1-oxopropyl)-1H-pyrazole-5-carboxylic acid A solution of 0.56 g of [1(S),5S]-4,5-dihydro-1-[3-(acetylthio)-2-methyl-1-oxopropyl]-1H-pyrazole-5-carboxylic acid in 5 ml of cold 6 N ammonium hydroxide is stirred in an argon atmosphere for 1 hour at room temperature. The solution is extracted with ethyl acetate and treated with 3 N hydrochloric acid to pH 2. The product is extracted twice with ethyl acetate, dried and evaporated to an oil which slowly solidifies during storage at 5° C. This material is dried in vacuo at 85° C. for several hours to remove a moderate amount of NH$_4$Cl. The yield of product is 0.28 g, melting point 108°-110° C., $[\alpha]_{20}{}^D = -171°$.

Analysis calc'd for C$_8$H$_{12}$N$_2$O$_3$S; C, 44.42; H, 5.59; N, 12.95; S, 14.82. Found: C, 44.15; H, 5.71; N, 12.88; S, 14.56.

EXAMPLES 3-5

Following the procedure of Example 1, but substituting the compound listed in column I for diazomethane and the compound listed in column II for D-3-(acetylthio)-2-methylpropionyl chloride, yields the compound listed in column III.

| | | |
|---|---|---|
| (3) diazoethane | D-3-(acetylthio)-2-(trifluoromethyl)propionyl chloride | [1(S),5S]-4,5-dihydro-1-[3-(acetylthio)-2-(trifluoromethyl)-1-oxopropyl]-3-methyl-1H-prazole-5-carboxylic acid |
| (4) 1-diazopropane | D-3-(acetylthio)propionyl chloride | [1(S),5S]-4,5-dihydro-1-[3-(acetylthio)-1-oxopropyl]-3-ethyl-1H-prazole-5-carboxylic acid |

| -continued | | |
|---|---|---|
| (5) 1-diazobutane | D-3-(benzoylthio)-2-methyl-propionyl chloride | [1(S),5S]-4,5-dihydro-1-[3-(benzoylthio)-2-methyl-1-oxopropyl]-3-(n-propyl)-1H-prazole-5-carboxylic acid |

EXAMPLE 6
[1(S),5S]-4,5-Dihydro-1-[3-(acetylthio)-2-methyl-1-oxopropyl]-5-methyl-1H-pyrazole-5-carboxylic acid (A)

Methyl-3,4-dihydro-5-methyl-5H-pyrazole-5-carboxylic acid

A solution of 10 g of methyl methacrylate in 100 ml of ether is treated with an excess of ethereal diazomethane for about 16 hours. The ether is removed in vacuo to give 12.5 g of the title compound as an oil. Examination of the oil on thin layer chromatography silica gel plates using 40% ethyl acetate/hexane shows a single spot at $R_f = 0.34$, visualized with phosphomolybdic acid plus heat. The oil has the following spectral characteristics: NMR($^{13}$C,CDCl$_3$ppm), 170.9(C-1), 94.1(C-2), 28.0(C-3), 77.1(C-4), 21.1(C-5), 52.3(C-6), IR(neat), 5.78μ(CO$_2$CH$_3$), 6.5μ(N=N).

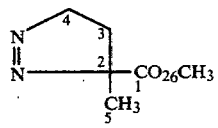

(B)

Methyl-4,5-dihydro-5-methyl-1H-prazole-5-carboxylic acid

A solution of 0.5 g of methyl-3,4-dihydro-5-methyl-5H-pyrazole-5-carboxylic acid in 10 ml of ether is treated with gaseous hydrogen chloride, rapidly forming an amorphous precipitate. After cooling for about 16 hours at 5° C., ether is decanted and the residue is washed several times with ether. The residue is dissolved in water, made basic with saturated sodium bicarbonate and extracted with ether. The ether extracts are washed with saturated brine, dried over anhydrous magnesium sulfate and concentrated to give 60 mg of product as an oil.

The original ether washes are washed with saturated sodium bicarbonate and saturated brine, dried over anhydrous magnesium sulfate and concentrated to give 260 mg of product identical to the 60 mg obtained above. Examination of the combined product on thin layer chromatography silica gel plates using 40% ethyl acetate/hexane shows a singel spot at $R_f = 0.34$, visualized with phosphomolybdic acid plus heat. The product has the following spectral characteristics: NMR($^{13}$C,CDCl$_3$,ppm), 175.2(C-1), 66.4(C-2), 43.6(C-3), 142.7(C-4), 23.5(C-5), 52.3(C-6).

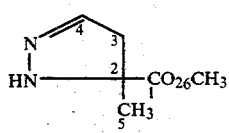

(C) 4,5-Dihydro-5-methyl-1H-prazole-5-carboxylic acid

A solution of methyl-4,5-dihydro-5-methyl-1H-pyrazole-5-carboxylic acid in chloroform is stirred with 1 N sodium hydroxide at room temperature for 5 hours. The aqueous layer is separated, acidified with 1.5 equivalents of hydrochloric acid and placed on a column of AG50W-X8 (H$^+$ form) ion exchange resin. The column is washed with water until neutral and the product is then eluted with 3 N ammonium hydroxide. Evaporation in vacuo yields the title compound.

(D)

[1(S),5S]-4,5-Dihydro-1-[3-(acetylthio)-2-methyl-1-oxopropyl]-5-methyl-1H-pyrazole-5-carboxylic acid Following the procedure of Example 1D, but substituting 4,5-dihydro-5-methyl-1H-pyrazole-5-carboxylic acid for 4,5-dihydro-1H-pyrazole-5-carboxylic acid, yields the title compound.

What is claimed is:

1. A compound having the formula

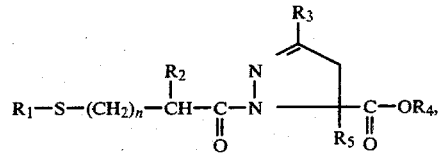

or a basic salt thereof, wherein
$R_1$ is hydrogen, alkyl, aryl, arylalkyl or

wherein $R_6$ is alkyl or aryl;
$R_2$ is hydrogen, alkyl, trifluoromethyl or pentafluoroethyl;
$R_3$ is hydrogen or alkyl;
$R_4$ is hydrogen, alkyl or arylalkyl;
$R_5$ is hydrogen or alkyl; and
n is 0, 1 or 2;
wherein the term "aryl" refers to phenyl or phenyl substituted with one, two or three halogen, alkyl, alkoxy, alkanoyl, nitro, amino, alkylamino, dialkylamino, trifluoromethyl, cyano or carboxyl groups; the terms "alkyl" and "alkoxy" refer to groups having 1 to 8 carbon atoms; and the term "alkanoyl" refers to groups having 2 to 9 carbon atoms.

2. A compound in accordance with claim 1 wherein $R_1$ is hydrogen.

3. A compound in accordance with claim 1 wherein $R_1$ is

4. A compound in accordance with claim 1 wherein R$_2$ is methyl.

5. A compound in accordance with claim 1 wherein R$_4$ is hydrogen.

6. A compound in accordance with claim 1 wherein n is 1.

7. The compound in accordance with claim 1 [1(S),5S]-4,5-dihydro-1-[3-(acetylthio)-2-methyl-1-oxopropyl]-1H-pyrazole-5-carboxylic acid.

8. The compound in accordance with claim 1 [1(S),5S]-4,5-dihydro-1-(3-mercapto-2-methyl-1-oxopropyl)-1H-pyrazole-5-carboxylic acid.

* * * * *

UNITED STATES PATENT AND TRADEMARK OFFICE
CERTIFICATE OF CORRECTION

PATENT NO. : 4,266,065
DATED : May 5, 1981
INVENTOR(S) : George C. Rovnyak

It is certified that error appears in the above-identified patent and that said Letters Patent are hereby corrected as shown below:

In column 10, Claim 3, the structure should read:

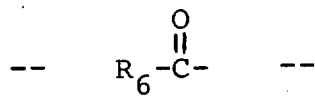

Signed and Sealed this

Third Day of November 1981

[SEAL]

Attest:

GERALD J. MOSSINGHOFF

Attesting Officer

Commissioner of Patents and Trademarks